United States Patent [19]

Djordjevich et al.

[11] Patent Number: 4,532,130
[45] Date of Patent: Jul. 30, 1985

[54] PREPARATION OF SYNTHETIC ERYTHROCYTES

[75] Inventors: Ljubomir Djordjevich, Chicago; Anthony D. Ivankovich, Glenview; William Gottschalk, Winnetka, all of Ill.

[73] Assignee: Rush-Presbyterian-St. Luke's Medical Center, Chicago, Ill.

[21] Appl. No.: 480,409

[22] Filed: Mar. 30, 1983

Related U.S. Application Data

[63] Continuation-in-part of Ser. No. 420,102, Sep. 20, 1982, abandoned, which is a continuation of Ser. No. 280,441, Jul. 6, 1981, abandoned.

[51] Int. Cl.$^3$ .................. A61K 35/14; A61K 35/18
[52] U.S. Cl. ......................................... 424/101; 514/6
[58] Field of Search ............................... 424/177, 101

[56] References Cited

PUBLICATIONS

Djordjevich–Dissertation (1979), University Microfilms Internat. (1981), 7925989.
Djordjevich–Dissertation Abst. Int. B, (1979), vol. 40, No. 5, p. 2281.
Remington's Pharmaceutical Sciences 16th edition, (1980), pp. 1454–1457.
Szoka–Ann. Rev. Biophys. Bioeng., vol. 9, (1980), pp. 467, 485 & 486.

*Primary Examiner*—Sam Rosen
*Attorney, Agent, or Firm*—Fitch, Even, Tabin & Flannery

[57] ABSTRACT

A sterile preparation of synthetic erythrocytes consisting of hemoglobin fraction encapsulated within water-immiscible amphiphylic membranes provides a total hemoglobin of at least about 12 gm percent at a hematocrit of 50%. A lipid composition is prepared and dispersed by agitation in a sterile, stroma-free 30–45 gram percent hemoglobin fraction. The dispersion is pressurized to between about 400 to about 900 kg/cm$^2$, and the pressure is substantially instantaneously released by passing the mixture to a lower pressure region through an orifice having an area of between about 0.1 and about 10.0 mm$^2$, thereby forming the synthetic erythrocytes. The preparation is filtered through a filter which passes particles having a diameter less than about 0.22 micron to eliminate any monocellular organisms that may be present and to eliminate larger synthetic erythrocytes.

The synthetic erythrocyte preparation, if dried under vacuum to remove the major portion of the water from the encapsulated hemoglobin fraction, substantially transforms the erythrocytes but retains the integrity of the encapsulating lipid composition membranes. In the dried form, the sterile erythrocytes are storable for extended periods.

11 Claims, 4 Drawing Figures

PREPARATION OF SYNTHETIC ERYTHROCYTES

This is a continuation-in-part of U.S. patent application Ser. No. 420,102, filed Sept. 20, 1982 which is a continuation of U.S. patent application Ser. No. 280,441 filed July 6, 1981, both now abandoned. The present invention relates to synthetic erythrocytes and methods of preparing the same.

BACKGROUND OF THE INVENTION

Erythrocytes are the red cells of blood which serve the biological function of transporting respiratory gases. In nature, the walls of the red cells are membranes which contain many different kinds of proteins and lipid materials. Oxygen passes through the erythrocyte walls and is exchanged for carbon dioxide which the erythrocytes carry away from the tissue.

It has long been common in the practice of medicine to take blood from a donor and transfuse this into the blood circulatory system of a patient who is deficient in hemoglobin. There are, however, difficulties in the preparation of blood for transfusion and substantial difficulties in maintaining adequate reserves of whole blood and/or blood components for transfusion.

One difficulty is that the natural erythrocytes in the blood of animals and humans deteriorate relatively soon after the blood is drawn, and present regulations require that the blood must be used for human transfusion within 21 days after it is drawn. Another serious inconvenience is that the blood of the donor must be typed and transfusions generally made into subjects whose blood is of the same type as that of the donor. Both of these disadvantages are due to the presence of proteins which are contained within the membranes of the natural erythrocytes.

U.S. Pat. No. 4,133,874 discloses a process in which a lipid in an organic solvent is spun to form a film on the interior walls of a container, and this film allowed to dry. Stroma-free hemoglobin is added, and by the use of ultrasound, hemoglobin is encapsulated within lipid composition membranes to form synthetic erythrocytes.

The '874 patent teaches that synthetic erythrocytes having hemoglobin solution encapsulated in lipid composition membranes can be used to transport respiratory gases in warm blooded animals; however, one with knowledge of the function of erythrocytes would recognize that improvements over the preparations described in the '874 patent might greatly enhance their utility.

The sonification method in the '874 patent is useful for producing synthetic erythrocytes under laboratory conditions but is not readily adaptable to mass production techniques. Importantly, the sonification method presents obstacles to providing and maintaining sterility of the preparation.

The most concentrated hemoglobin fraction encapsulated in the disclosure of the '874 patent is 22 gram percent hemoglobin, i.e., about two-thirds the concentration of hemoglobin within the erythrocytes of healthy humans. Using this concentration of hemoglobin, the preparation at a 50 percent hematocrit (slightly greater than normal whole blood) is necessarily less than 12 percent, and accounting for the synthetic erythrocyte membranes and the void volume between packed cells, the total hemoglobin at 50 percent hematocrit would not be more than about 9 gram percent. This compares quite unfavorably with the total hemoglobin of about 15 gram percent found in normal human blood.

The synthetic erythrocytes formed by the sonification process described in the '874 patent have a range of diameters of from about 0.1 microns to about 10 microns. The upper end of this size range is generally unsuitable for transfusion into warm blooded animals, being too large to fit through capillaries (human erythrocytes have a diameter of about 7 microns). Synthetic erythrocytes should be somewhat smaller than natural erythrocytes because synthetic erythrocytes are less flexible and do not pass as easily through the constricted capillaries. Several advantages accrue by providing synthetic erythrocytes within a narrow size range at the lower end of the size range described in the '874 patent.

An essential attribute of a synthetic erythrocyte preparation for transfusion into animals, and particularly humans, is that the preparation be sterile. The introduction of a synthetic erythrocyte preparation represents a dilution of infection-resistant agents normally present within blood, including antibodies produced by lymphocytes. In any case, a synthetic erythrocyte preparation should not introduce infectious agents. Synthetic erythrocyte preparations cannot be sterilized by heat or any other sterilization method which would denature the hemoglobin or destabilize the synthetic erythrocyte membranes.

An important projected use of synthetic erythrocytes preparations is to substitute for whole blood in remote locations where there is no readily available source of fresh blood. Whereas the shelf life of blood is about 21 days under refrigeration, synthetic erythrocyte preparations may be stored for considerably longer periods. It would be desirable to have synthetic erythrocytes which may be stored substantially indefinitely even when not refrigerated.

SUMMARY OF THE INVENTION

The present invention provides a preparation of sterile synthetic erythrocytes having a total hemoglobin concentration of at least about 12 gram percent at a hematocrit of 50 percent. A water-immiscible composition is prepared which is between about 60 and about 90 weight percent lipids, between about 10 and about 40 weight percent of a sterol and between 0 and about 10 weight percent of an agent that imparts a negative charge to the surface of the composition. A stroma-free hemoglobin fraction is separated from whole blood, and its hemoglobin concentration is adjusted to between about 30 and about 45 gram percent. The water-immiscible amphiphylic composition and hemoglobin fraction are mixed at a volume ratio of between about 1:3 and about 1:10, and the mixture is agitated to disperse globules of the water-immiscible composition less than about 1 mm in diameter within the hemoglobin fraction. The resultant dispersion is pressurized to a gage pressure of between about 450 kg/cm$^2$ and about 900 kg/cm$^2$, and the pressurized dispersion is subjected to high shear conditions by passing it through an orifice having a cross-sectional area of between about 0.05 mm$^2$ and about 10.0 mm$^2$ to substantially instantaneously release the pressure, thereby forming a preparation of synthetic erythrocytes in which hemoglobin fraction is encapsulated within outer membranes of the lipid composition. The preparation is filtered through a filter having a pore size that passes particles having a maximum diameter of below about 0.22 micron.

DETAILED DESCRIPTION OF THE PREFERRED EMBODIMENTS

Figure 1:
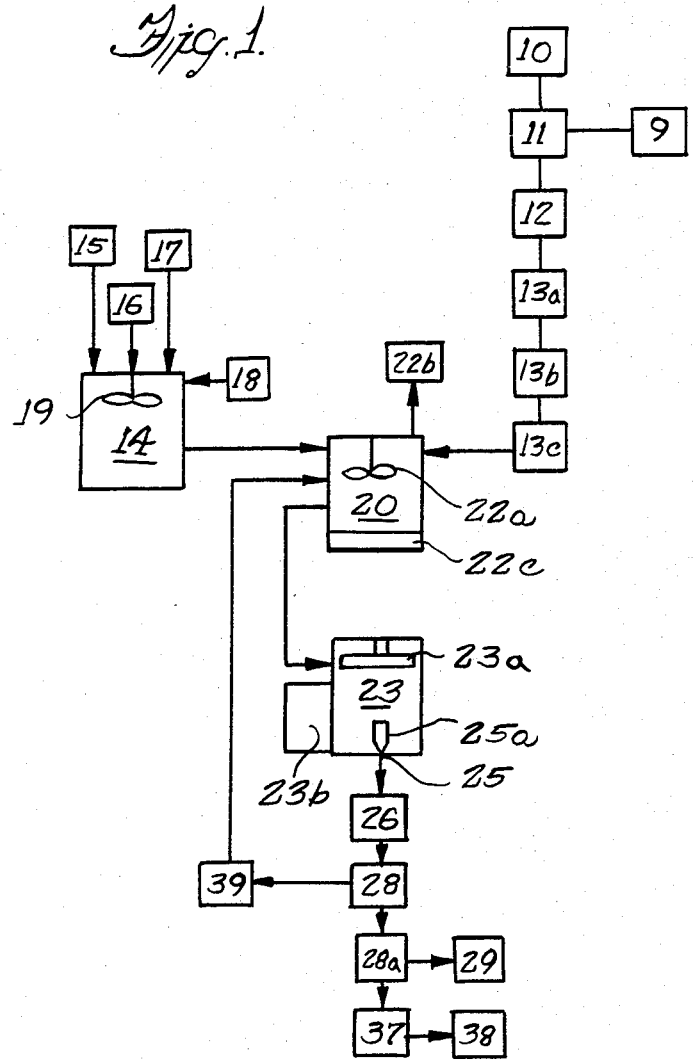
FIG. 1 is a schematic flow diagram of the process of the present invention.

Herein the term "synthetic erythrocyte" is used to refer to a tiny spheroid in which hemoglobin fraction is encapsulated in a lipid composition membrane.

The term "lipid" refers to various materials that are soluble in non-polar solvents, including fats, waxes, phosphatides, cerebrosides, and related and derived compounds which constitute the principle structural components of the living cell. The lipids used herein may be obtained from a wide variety of sources. A lipid composition is selected which does not induce immunological responses in a host mammal.

It is believed that lipid composition encapsulation of a hemoglobin fraction is a surface related effect in which polar moieties of the lipids face inward to the encapsulated hemoglobin fraction and outward to the free hemoglobin fraction while non-polar moieties aggregate centrally within the membrane. It is believed that lipid membranes formed by the processes of the invention are two molecules thick with non-polar ends of lipid molecules joined end-to-end. The lipid composition must have sufficient polar moieties to form the membrane, and it is preferred that the phospholipids comprise at least about 50% by weight of the lipid composition. Lecithin is a preferred lipid composition for forming the lipid membrane being high in phospholipid content and generally free of immune response-inducing agents.

The lipid composition preferably incorporates a sterol, such as cholesterol, to enhance the mechanical strength of the synthetic cell membrane. The sterol is preferably present in amounts of between about 10% and about 40% by weight of the lipid composition.

The lipid composition may incorporate an agent to adjust the charge of the lipid composition and thereby the charge of the synthetic cell surface. The surface of a natural erythrocyte is negatively charged, a feature which prevents aggregation of the cells. The zeta potential of a natural erythrocyte is about 18 millivolts, and that the zeta potential of the synthetic erythrocyte may be adjusted to between about 7 and about 23 millivolts. Suitable agents for adjusting the charge include phosphatidic acid, dicetyl phosphate and pharmaceutically acceptable salts thereof. The charge adjusting agent may comprise from 0 up to about 10 weight percent of the lipid composition.

The lipid composition is prepared by dissolving its various components in an organic solvent or a mixture of solvents, such as chloroform, chloroform-methanol mixture or dichloromethane, to produce a homogeneous mixture, and thereafter, the organic solvent is evaporated away. The organic solvent system is selected to destroy infectious agents present in the lipid compositions. It is desirable to substantially remove the solvent prior to admixture with hemoglobin lest the solvent denature the hemoglobin. The lipid composition has a paste-like consistency.

Hemoglobin is obtained from washed red blood cells lysed by conventional means. The cells are washed by repeated suspensions in isotonic saline (or balanced salt solutions) followed by centrifugation to pack the cells. Mechanical methods, such as freezing and thawing the cells, ultrasonic disruption of the membranes hypotonic lysing, or high pressure (70–210 kg/cm$^2$) disruption are generally preferred to chemical membrane disruption methods so that the amount of hemoglobin denaturization is minimized. The cells may, however, be chemically lysed by toluene, a solvent which does not denature hemoglobin.

In one method of separating the stroma from the hemoglobin of the lysate, the pH of the lysate is reduced from the physiological pH of about 7.4 to below about 5.0 where the stroma readily precipitates out by centrifugation. A clear, concentrated hemoglobin solution is obtained by filtration which removes remaining cell solids. Alternatively, stroma may be removed by ultrafiltration, e.g., through 100,000 pore size filter.

The gas transport capacity of the synthetic erythrocyte preparation is a function of the total amount of encapsulated hemoglobin. It is desirable that the total amount of encapsulated hemoglobin per volume of synthetic erythrocyte preparation approach or even exceed the total amount of hemoglobin encapsulated in a similar volume of natural erythrocytes, and for purpose of this invention, a synthetic erythrocyte preparation should provide a total hemoglobin of at least about 12 gram percent at a hematocrit of 50 percent. The preferred size range of the erythrocytes in the preparation is between about 0.05 and about 0.2 micron in diameter. To achieve a total hemoglobin level approaching that of normal blood, it is preferred that the hemoglobin fraction used for encapsulation be at the high end of the hemoglobin concentration range (28–33 weight percent) found within natural erythrocytes and preferably even higher. Highly concentrated hemoglobin solutions, however, are quite viscous making them difficult to encapsulate, and a fifty gram percent hemoglobin fraction represents the most highly concentrated solution that can be generally be encapsulated. For purposes of the invention, it is preferred that the hemoglobin concentration of the hemoglobin fraction be between about 30 and about 45 weight percent.

Where a more highly concentrated hemoglobin fraction is desired than is obtainable from cell lysis, it is necessary to concentrate the hemoglobin. The hemoglobin may be concentrated by filtering the hemoglobin fraction with a filter having a pore size sufficient to pass water and other small molecules, e.g. about 10,000 MW filter, but retaining the larger molecules. The hemoglobin fraction might also be concentrated by evaporating water, e.g., through lyophilization; however, if the water is withdrawn, it is also desirable to remove a corresponding amount of electrolytes so that the encapsulated hemoglobin fraction is not unduly high in electrolyte concentration causing it to draw in water through osmosis, expanding and possibly lysing the lipid composition membrane.

It is important that the hemoglobin be sterile lest the artifical erythrocytes introduce infection to the transfused animal. Excess heat, of course, would denature the hemoglobin. In above-mentioned U.S. Pat. No. 4,133,874, bacteriostatic agents, such as gentamycin and tetracycline, were added to the hemoglobin solution. While such agents may be added, their use is preferably avoided because the product erythrocytes are intended to be generally acceptable to all recipients, and bacteriostatic agents may induce allergic response in certain patients. A preferred method of sterilizing the hemoglobin solution is by passing the solution through a membrane permeable by hemoglobin but impermeable to living cells. Such a membrane has a pore size which permits passage of particles less than about 0.22 microns in diameter. Suitable membranes for this purpose are sold by Nuclepore and Millipore.

The lipid composition is dispersed in the hemoglobin solution by blending with a high speed mixer to break the lipid composition into globules having an average size less than about 1 mm in diameter. The ratio of lipid composition to hemoglobin fraction is not critical, the ratio affecting efficient utilization of the components more than erythrocyte production. However, the volume ratio of hemoglobin fraction to lipid composition should be greater than about 3:1 or else significant amounts of lipid spheroids will be formed having no encapsulated hemoglobin. On the other hand, a large excess of hemoglobin fraction is wasteful of hemoglobin and increases the required capacity of hemoglobin recycling systems. A preferred volume ratio of hemoglobin fraction to lipid composition is between about 5:1 and about 10:1.

At the high hemoglobin concentrations used to form the synthetic erythrocytes and within the preferred volume ratio range of hemoglobin fraction to lipid compositions, quite viscous dispersions are formed. For example, a dispersion of 35 gm % hemoglobin solution mixed at a 10:1 volume ratio with a lipid composition comprising 40.7 g lecithin, 20.7 g cholesterol, and 6.9 g dicetyl phosphate is found to have a viscosity of 982 centipoise at 37° C. and 1640 centipoise at 4° C., as measured using a Brookfield cone plate viscometer with a CP-42 cone and cone angle of 1.565 degrees and shear rate of 1.15 sec$^{-1}$. Dispersions in accordance with this invention have viscosities, as measured above, of from about 1500 to about 3200 centipoise at 4° C. The actual viscosity of each dispersion depends on several factors including the concentration of the hemoglobin fraction, the specific lipid composition, the volume ratio of hemoglobin fraction and lipid composition and the size of the dispersed lipid composition particles. The sonification method used for hemoglobin encapsulation in the above-mentioned 4,133,874 patent would be generally ineffective for encapsulating hemoglobin dispersions having such high viscosities.

In accordance with the present invention, synthetic erythrocytes are formed from a hemoglobin fraction-lipid composition dispersion by subjecting the dispersion to substantial pressures and substantially instantaneously releasing the pressure.

According to one method of forming the erythrocytes, the dispersion is pressurized, e.g., by mechanical means, to between about 400kg/cm$^2$ and about 900 kg/cm$^2$, and preferably between about 450kg/cm$^2$ and about 700kg/cm$^2$. The pressurized dispersion is then passed through a restricted orifice or nozzle at high velocity to a region of lower pressure, thereby subjecting the dispersion to substantial shear forces which results in creation of the synthetic erythrocytes having thin lipid membranes encapsulating hemoglobin fraction.

Another method of pressurizing the lipid-hemoglobin dispersion is by introducting a pressurized inert gas, such as nitrogen, into the vessel containing the dispersion. When the pressure is substantially instantaneously released by passing the gas-infused mixture through a restricted orifice, synthetic erythrocytes are formed.

The shear force to which the dispersion is subjected is an important factor in determining the size distribution of the synthetic erythrocytes of the preparation. The size distribution of the erythrocytes of the preparation depends on several factors including the pressure, the orifice area, and the viscosity of the dispersion. At the present time, there does not exist a precise correlation of these factors with synthetic erythrocytes size distribution; however, it is known that the higher the pressure, the larger the permissible size of the orifice that will produce the necessary shear force to obtain predominantly monolaminar synthetic erythrocytes. Generally, within the above-described pressure ranges, the orifice size should be between about 0.1 square millimeter and about 10 square millimeters. For a given lipid composition and a given hemoglobin fraction, the pressure and orifice size may be adjusted to obtain a desired size distribution.

For purposes of this invention, it is preferred that about 80 percent of the erythrocytes produced have a diameter within a 0.05 to 0.2 micron range. The small synthetic erythrocytes in this size range have high surface-to-volume ratios that increase gas exchange through the membrane, and synthetic erythrocytes of this size range have less tendency to aggregate than larger synthetic erythrocytes. Using synthetic erythrocytes less than about 0.2 micron in diameter reduces or eliminates the tendency of the synthetic erythrocytes to lodge within the capillaries. This small size range is also highly desirable for perfusion of ischemic tissue.

Although larger size synthetic erythrocytes might be expected to have greater hemoglobin fraction to lipid composition membrane volume ratios, it is believed that larger synthetic erythrocytes tend to have multilaminar membranes negating this apparent advantage. It is found experimentally that the greatest amount of hemoglobin encapsulation occurs in the 0.05–0.2 micron diameter range which corresponds closely to the size of the majority of cells produced by the methods of the present invention. Below about 0.05 microns, the small size tends to substantially decrease the hemoglobin to lipid membrane volume ratio.

Previous teachings of lipid encapsulation of aqueous solution suggest that single membrane layer liposomes have a diameter range of between about 0.02 and about 0.05 micron, whereas liposomes may be formed between 0.1 and 10 microns having multilaminar membranes. Suprisingly and unexpectedly, using lipid compositions and hemoglobin solutions with the above-described parameters and processing them within the above-described pressure and orifice size ranges, the tendency is to form liposomes that are predominantly in the 0.05 to 0.2 micron diameter size range and which, based upon the measured total hemoglobin of the preparation, appear to be predominantly monolaminar.

After the synthetic erythrocytes are prepared, they are again passed through a filter that does not permit passage of particles having diameters greater than 0.22 microns in order to remove any unicellular infectious agents which were not previously removed or destroyed or which might have been later introduced. This filtering process also removes the small percentage of larger synthetic erythrocytes.

In accordance with an important aspect of the present invention, it is found that the synthetic erythrocytes may be dried under vacuum to remove a major portion of the water content and that when so dried, the configuration of the synthetic erythrocytes changes dramatically. The dried synthetic erythrocytes may be stored for greatly extended periods of time and reconstituted merely by adding water or an aqueous solution.

Despite the encapsulation of highly colored hemoglobin, the synthetic erythrocytes cannot be clearly seen under an optical microscope, the lipid membranes diffusing light so that a clear image cannot be seen. However, when the synthetic erythrocytes are dried to where the water concentration in the encapsulated hemoglobin fraction is below about 50 weight percent, the surface conditions which created the synthetic erythrocytes are substantially altered, and the synthetic erythrocytes undergo a transition. The transformed synthetic erythrocytes are readily distinguishable from the original synthetic erythrocytes, being easily seen under an optical microscope appearing as red spheroids. Thus, suprisingly, the lipid membranes remain intact even though the conditions of surface interaction, under which the membranes were created, are radically changed. Furthermore, it is found that the dried spheroids are reconstitutable into their original form merely by adding aqueous solution. In dried form, the synthetic erythrocytes are highly resistant to degradation and may be stored for long periods of time. For long-term storage, it is preferred that the water content of the synthetic erythrocytes be reduced to below about 10% by weight of the hemoglobin fraction and more preferably to below about 1% by weight of the hemoglobin fraction.

Referring now in greater detail to the schematic diagram (FIG. 1) representing one mode of practicing the invention, squares or blocks are used to represent steps or units of equipment.

Beginning at the top of FIG. 1, a washing saline solution from a container 10 and whole blood from container 9 are passed through a centrifuge 11 used to separate plasma from whole blood. The blood may have been drawn from humans or from other mammals. The plasma is separated off, and the fraction containing the red blood cells, or erythrocytes, is passed to a cell lysing apparatus 12 where the natural erythrocytes are subjected to high pressure to rupture the cell membranes after which the membranes and any tissue solids are removed by ultrafiltration at unit 13a, leaving a stroma-free hemoglobin fraction. The ultrafiltration also removes particles any cellular infectious agents. A unit 13b is used to concentrate the hemoglobin fraction to between about 30 and about 45 gram percent. The sterile, stroma-free hemoglobin is held in a sealed receptacle 13c.

Turning now to the left-hand side of FIG. 1, there is a mixing vessel 14 into which a quantity of a lipid material is fed from a container 15. There is also added sterol, such as cholesterol, from a container 16, and a surface charge-adjusting agent, such as dicetyl phosphate, is added from a container 17 to give the mixture the desired electrical charge. A 9:1 v/v chloroform-methanol solution is added from a container 18. The phospholipid, sterol, and dicetyl phosphate are dissolved in the solvent using a mixer 19.

The resulting non-polar solution is fed into a mixing vessel 20 having an associated agitator 22a, a vacuum source 22b and heater 22c. The heater 22c mildly heats the solution while the vacuum source 22b draws off all of the solvent leaving a sterile lipid composition. The lipid composition is cooled to about 10° C., and hemoglobin solution from vessel 13c is introduced.

As the hemoglobin solution is introduced, the agitator 22a is actuated breaking the lipid composition into globules which disperse within the hemoglobin solution. Agitation is continued until substantially all of the lipid composition is broken into globules less than about 1 mm in diameter.

From the mixing vessel 20, the dispersion is passed to a compression chamber 23 having a piston 23a, and one or more orifices 25 having an associated valve 25a. The compression chamber 23 has associated cooling apparatus 23b to cool the dispersion to between about 20° C. and 0° C.

Figure 2:
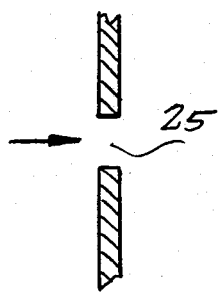
FIG. 2 is a view in cross section of one type of orifice which may be used to effect encapsulation of stroma-free hemoglobin within phospholipid membranes.
Figure 3:
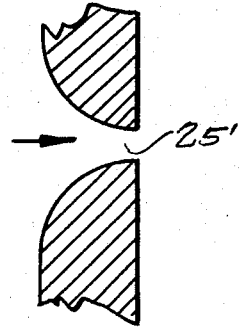
FIG. 3 is a view in cross section of another type of orifice which may be used.
Figure 4:
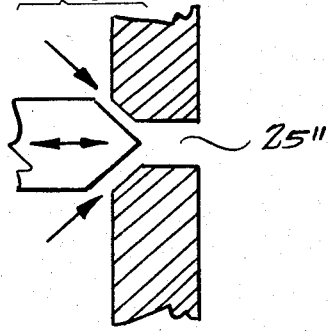
FIG. 4 is a sectional view of yet another type of orifice which may be used in the practice of the invention.

The orifice 25 may be of the type illustrated in either of FIG. 2, FIG. 3, or FIG. 4. The type 25 illustrated in FIG. 2 is an ordinary circular orifice in the wall of a vessel. The type 25' shown in FIG. 3 is like that shown in FIG. 2 but with rounded corners at the edge of the orifice which causes the orifice to resemble that which is found in a common nozzle. The type 25" shown in FIG. 4 is a variable orifice.

The piston 23a is actuated until the dispersion is sufficiently pressurized. As stated above, the required pressure depends on the viscosity of the dispersion and the particular orifice size. After the dispersion is fully pressurized, the valve 25a is actuated opening the orifice 25, resulting in the dispersion being expelled from the compressing chamber 23 into a collecting receptacle 26. As the lipid globules pass through the orifice at high speed, they are subjected to very high shear forces, and the dispersion emerges from the orifice 25 in the form of synthetic erythrocytes having lipid composition membranes encapsulating hemoglobin solution, the synthetic erythrocytes being suspended in the remaining hemoglobin solution.

The synthetic erythrocytes from receptacle 26 are preferably washed by addition of a balanced salt solution. The synthetic erythrocytes are filtered in a unit 28 to remove unencapsulated hemoglobin solution from the synthetic erythrocytes. Then the synthetic erythrocytes are passed through a second filter 28a to reassure removal of any bacteria and remove any oversize synthetic erythrocytes. The filtered synthetic erythrocytes may be used, as packed cells as constituted, for transfusion as a product, or may be dried in a vacuum unit 29 for storage as packed cells and use at a later date.

The filtered synthetic erythrocytes are suspended in a vessel 37 in a plasma-like solution, such as balanced salt solution to which albumin is added. This suspension may be directly transfused as a whole blood substitute into a mammalian animal, or may be dried in a vacuum unit 38 for storage as reconstitutable artificial blood.

The diluted hemoglobin solution, obtained as a by-product of washing the synthetic erythrocytes at the filtering unit 28, may also be passed under pressure through a filter 39 having a pore size, e.g., 1000 MW, that retains the hemoglobin but allows passage of the water and small dissolved molecules in order to concentrate the recovered hemoglobin. The concentrated stroma-free hemoglobin is reintroduced along with fresh stroma-free hemoglobin into the mixing vessel 20.

Figure 1A:
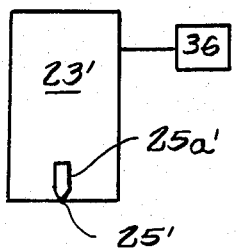
FIG. 1A is schematic flow diagram of those portions of an alternate embodiment of the process that differs from the process illustrated in FIG. 1.

In a modified process, the modified steps being represented in FIG. 1A, the compression chamber 23' is associated with a source 36 of inert gas, such as nitrogen. In this modified process, the nitrogen, or other inert gas, is pumped from source 36 into the compressing chamber 23' and much of the gas is absorbed into the lipid and water in hemoglobin fraction dispersion in the compression chamber 23'. When a valve 25a' is opened so that the mixture containing the absorbed gas emerges rapidly from the orifice 25' with a sudden drop in the applied pressure, synthetic erythrocytes are formed as before.

Following are specific examples which described carrying out the invention:

EXAMPLE 1

A lipid composition is prepared by dissolving 40.7 grams of egg lecithin, 20.7 grams of cholesterol and 6.9 grams of dicetyl phosphate in 200 ml of a 9:1 v/v chloroform-methanol mixture. In a mixing vessel equipped with a heater, a stirrer, and a vacuum, the solvent drawn off with heat and vacuum.

A hemoglobin fraction is obtained by lysing washed, packed erythrocytes and removing the stroma. The hemolysate is determined to have 29 gm percent hemoglobin. 20 gm percent hemoglobin solution is obtained by diluting the hemolysate with a balanced salt solution. 30 and 40 gram percent hemoglobin solutions are obtained by exposing the hemolysate to a filter which allows passage of water and electrolytes but which retains the hemoglobin. The remaining steps of the process are performed three times, once with each concentration (20, 30 and 40%) of hemoglobin fraction.

The hemoglobin fraction is passed through a filter that permits passage of particles having diameters of 0.22 microns or less, and 200 ml of filtered hemoglobin fraction is introduced into the mixing vessel. The agitator within the vessel is activated spinning a blade at 16,000 rpm for 15 minutes to disperse the lipid composition as small globules within the hemoglobin fraction.

The dispersion is transferred to a compression chamber having a piston to reduce the volume and a valved circular orifice 1 mm in diameter. The piston is mechanically driven, creating a pressure of 700 kg/cm$^2$, and then the valve is opened allowing the dispersion to escape to a receptacle.

The resulting preparation contains synthetic erythrocytes suspended in the remainder of the hemoglobin fraction. The preparation is filtered to remove non-encapsulated hemoglobin fraction and the preparation is washed to remove all remaining hemoglobin. At this point, a sample of synthetic erythrocytes is removed from the washed, filtered preparation, and the size of the synthetic erythrocytes determined by freeze fraction electron microscopy. The following data represents the size distribution of the synthetic erythrocytes prepared using the 20, 30, and 40 gram percent hemoglobin fractions. Cell Size distribution as determined by electrom microscopy.

| Concentration of Hemoglobin Fraction | 20 gm % | 30 gm % | 40 gm % |
|---|---|---|---|
| number of cells counted | 283 | 293 | 397 |
| Mean diameter (microns) | .1802 | .1316 | .1221 |
| Standard deviation | .0999 | .0753 | .0752 |
| Min. diameter | .0074 | .0074 | .0074 |
| Max. diameter | .7037 | .5852 | .5852 |
| percent below 0.22 microns | 79.5 | 93.6 | 97.9 |
| Concentration of Hemoglobin Fraction in size | 20 gm % | 30 gm % | 40 gm % |

The preparation is passed through a filter that allows passage of particles of about 0.22 microns or less, removing any monocellular microorganism and larger synthetic erythrocytes. The total hemoglobin is determined for the preparation from each hemoglobin solution, and the total hemoglobin at a fifty percent hematocrit for the 20 gram percent fraction is 9 gram percent, for the 30 gram percent fraction preparation 14 and for the 40 gram percent fraction 19. The total hemoglobin in each case corresponds closely to the theoretical amount of hemoglobin encapsulated if all of the synthetic erythrocytes have monolaminar membranes.

This experiment demonstrates that a sterile synthetic erythrocyte preparation can be produced according to the present invention having a total hemoglobin within the range of natural erythrocytes.

EXAMPLE 2

A dispersion of lipid globules in a 30 gm percent hemoglobin fraction is produced as in Example 1. The dispersion is transferred to a compression chamber with an associated source of pressurized nitrogen and a 1 mm. diameter orifice. The chamber is communicated to the source of pressurized nitrogen to raise the pressure in the chamber to 450 kg/cm$^2$. The valve is then opened to release the pressurized dispersion through the orifice.

The resulting preparation is washed and filtered to remove larger erythrocytes and any infectious agents. The washed and filtered erythrocyte preparation has a 12 gram percent total hemoglobin concentration at a 50% hematocrit.

EXAMPLE 3

The synthetic erythrocytes prepared in Example 1 from the 30 gram percent hemoglobin fraction are packed and subjected to vacuum conditions at 4° C. until no further weight loss is detected. The water concentration is determined to be less than 1 weight percent of the encapsulated hemoglobin. The synthetic erythrocyte suspension is examined under a microscope before and after drying. No clear image of cells is produced in the wet preparation. Dried synthetic erythrocyte suspension appears as red spheroids. Thus, it is demonstrated that synthetic erythrocytes, produced in accordance with this invention, undergo a substantial transformation when they are dried.

The dried synthetic erythrocyte preparation is reconstituted with balanced salt solution. A determination of the free hemoglobin in the reconstituted suspension shows that less than about 5 percent of the hemoglobin is freed during lyophilization and reconstitution.

EXAMPLE 4

The washed synthetic erythrocyte prepared in Example 1 from the 30 gm percent hemoglobin fraction is suspended in equal volume of Ringer's solution containing 5 volume percent albumin.

40 ml of the resulting synthetic erythrocyte suspension is administered to a rat by a technique wherein an infusion pump is employed to effect simultaneous withdrawal of blood from the femoral artery and infusion of the synthetic erythrocyte suspension into the femoral vein. All 40 ml of suspension (approximately 250% of the rat's natural blood volume) is administered over a period of 3 hours. The rat survives the transfusion for more than 24 hours and eventually dies of bacterial infection (septic shock).

Described in the foregoing description are certain embodiments of the invention, but it is understood that our invention may be embodied in various forms, and many changes may be made, all within the spirit of the invention. For example, the hemoglobin fraction with dispersed lipid composition may be passed under pressure through as orifice several times.

Various features of the invention are set forth in the following claims.

What is claimed is:

1. A process for producing a sterile synthetic erythrocyte preparation providing a total hemoglobin concentration of at least 12 gram percent when suspended in a liquid medium to a hematocrit of 50 percent, the process comprising Preparing a water-immiscible composition comprising between about 60 and about 90 weight percent lipids, between about 10 and about 40 weight percent of a sterol and between 0 and about 10 weight percent of an agent that imparts a negative charge to the surface of said composition, separating from whole blood a stroma-free hemoglobin fraction, adjusting the concentration of said stroma-free hemoglobin fraction to between about 30 and about 45 gram percent, mixing said adjusted hemoglobin fraction with said water-immiscible composition at a hemoglobin fraction to lipid composition volume ratio of between about 3:1 and about 10:1, agitating said mixture to disperse globules of said water-immiscible composition within said hemoglobin fraction, pressurizing said dispersion to a gauge pressure of between about 400 kg/cm$^2$ and about 900 kg/cm$^2$, passing said pressurized dispersion through an orifice having a cross-sectional area of between about 0.1 mm and about 10.0 mm to substantially instantaneously release the pressure and thereby to form a preparation of synthetic erythrocytes having hemoglobin fraction encapsulated within membranes of said composition, the gauge pressure being selected according to the orifice size so as to obtain synthetic erythrocytes primarily in the 0.05 micron to 0.02 micron size range, filtering said composition through a filter which passes particles having a diameter about 0.22 micron in diameter or less, thereby removing microorganisms from the preparation.

2. A process according to claim 1 wherein said dispersion is pressurized to a gage pressure of between about 450 and about 700 kg/cm$^2$.

3. A process according to claim 1 including adjusting said gage pressure according to the diameter of said orifice to produce a synthetic erythrocyte preparation wherein at least about 80 percent of said synthetic erythrocytes have diameters between about 0.05 micron and about 0.2 micron in diameter.

4. A process according to claim 1 including filtering said preparation to separate free hemoglobin fraction from said synthetic erythrocytes preparation.

5. A process according to claim 4 including recovering hemoglobin from said separated hemoglobin fraction by filtering said medium through a hemoglobin-impermeable membrane.

6. A process according to claim 1 wherein said dispersion is pressurized by reducing the volume of the vessel in which said dispersion is contained.

7. A process according to claim 1 wherein said dispersion is pressurized by introducing a pressurized gas into the vessel wherein said lipid composition is contained.

8. A process according to claim 6 including drying said synthetic erythrocytes under vacuum to reduce the water content of said encapsulated hemoglobin fraction.

9. A process according to claim 1, said dispersion having a viscosity at 4° C. of between about 1500 centipoise and about 3200 centipoise as measured with a Brookfield cone plate viscometer with a CP-42 cone and a cone angle of 1.565 degrees, and using a shear rate of 1.15 sec$^{-1}$.

10. A process according to claim 5 including mixing said recovered hemoglobin with said stroma-free hemoglobin fraction to recycle unencapsulated hemoglobin.

11. A process for producing a dried reconstitutable synthetic erythrocytes comprising separating from whole blood a stroma-free hemoglobin fraction, mixing said stroma-free hemoglobin fraction with a lipid composition in a vessel, pressurizing the resulting mixture, substantially instantaneously releasing said pressure to form a suspension of synthetic erythrocytes in a portion of said hemoglobin fraction, said synthetic erythrocytes having hemoglobin fraction encapsulated in lipid membranes, separating said synthetic erythrocytes from said aqueous medium, and reducing the water content of said synthetic erythrocytes to less than 10% by weight of said encapsulated hemoglobin fraction.

* * * * *

UNITED STATES PATENT AND TRADEMARK OFFICE
CERTIFICATE OF CORRECTION

PATENT NO. : 4,532,130

DATED : 7-30-85

INVENTOR(S) : Djordjevich et al.

Page 1 of 2

It is certified that error appears in the above-identified patent and that said Letters Patent is hereby corrected as shown below:

Title Page, Title of Patent, Change "FRYTHROCYTES" to --ERYTHROCYTES--.

Column 1, line 2, change "FRYTHROCYTES" to --ERYTHROCYTES--.

Column 4, line 48, delete "be" first instance;
line 57, after "e.g." insert --,-- (comma).

Column 7, line 54, delete "particles".

Column 8, line 53, change "use" to --used--.

Column 9, line 13, change "described" to --describe--;
line 21, after "solvent" insert --being--;
line 59, change "electrom" to --electron--.

Column 10, line 57, change "lyophylization" to --lyophilization--;
line 60, change "preparared" to --prepared--.

Column 11, line 12, change "as" to --an--;
line 21, change "Preparing" to --preparing--;
line 49, change "0.02" to --0.2--.

UNITED STATES PATENT AND TRADEMARK OFFICE
CERTIFICATE OF CORRECTION

PATENT NO. : 4,532,130

DATED : 7-30-85

INVENTOR(S) : Djordjevich et al.

It is certified that error appears in the above-identified patent and that said Letters Patent is hereby corrected as shown below:

Column 12, line 50, after "than" insert --about--.

Signed and Sealed this

Tenth Day of December 1985

[SEAL]

Attest:

Attesting Officer

DONALD J. QUIGG

Commissioner of Patents and Trademarks